United States Patent
Chrysselis et al.

(10) Patent No.: US 6,693,192 B1
(45) Date of Patent: Feb. 17, 2004

(54) HYPOLIPIDEMIC AND ANTIOXIDANT MORPHOLINE DERIVATIVES

(75) Inventors: Michael Chrysselis, Thessaloniki (GR); Eleni Rekka, Thessaloniki (GR); Panagiotis Kourounakis, Thessaloniki (GR)

(73) Assignee: Elpen S.A., Pikermi Attica (GR)

( * ) Notice: Subject to any disclaimer, the term of this patent is extended or adjusted under 35 U.S.C. 154(b) by 0 days.

(21) Appl. No.: 09/869,881

(22) PCT Filed: Jan. 14, 2000

(86) PCT No.: PCT/GR00/00003

§ 371 (c)(1),
(2), (4) Date: Oct. 11, 2001

(87) PCT Pub. No.: WO00/42030

PCT Pub. Date: Jul. 20, 2000

(30) Foreign Application Priority Data

Jan. 14, 1999 (GR) .......................................... 990100015
Jul. 5, 1999 (GR) .......................................... 990100227

(51) Int. Cl.$^7$ ............................................ C07D 265/32
(52) U.S. Cl. ...................................... 544/106; 544/167
(58) Field of Search ................................. 544/106, 167

(56) References Cited

PUBLICATIONS

Tani et al (1994): Arzneim–Forsch Drug Res. vol 44, No. 9, 992–994.*

\* cited by examiner

Primary Examiner—Joseph K. McKane
Assistant Examiner—Golam M M Shameem

(74) Attorney, Agent, or Firm—Ladas & Parry

(57) ABSTRACT

The present invention relates to the synthesis and the evaluation of the antioxidant, hypocholesterolemic and hypolipidemic activity of substituted morpholine derivatives of formula (I) in which $R_1=CH_2CH_3$, $R_2=CH_3$, $R_3$, $R_4=H$, $R_5=C_6H_5$ (compound 1) or $R_1=CH_2CH_2CH_2ONO_2$, $R_2=CH_3$, $R_3$, $R_4=H$, $R_5=C_6H_5$ (compound 2) or $R_1=H$, $R_2$—$R_3=(CH_2)_4$, $R_4=H$, $R_5=C_6H_5$ (compound 3) or $R_1=CH_2CH_2CH_3$, $R_2$—$R_3=(CH_2)_4$, $R_4=H$, $R_5=C_6H_5$ (compound 4) or $R_1=CH_2CH_2CH_2ONO_2$, $R_2$—$R_3=(CH_2)_4$, $R_4=H$, $R_5=C_6H_5$ (compound 5) or $R_1=H$, $R_2=CH_3$, $R_3$—$R_4=(CH_2)_4$, $R_5=C_6H_5$ (compound 6) or $R_1=CH_2CH_2CH_3$, $R_2=CH_3$, $R_3$—$R_4=(CH_2)_4$, $R_5=C_6H_5$ (compound 7) or $R_1=CH_2CH_2CH_2ONO_2$, $R_2=CH_3$, $R_3$—$R_4=(CH_2)_4$, $R_5=C_6H_5$ (compound 8) or $R_1=CH_2CH_2CH_2ONO_2$, $R_2=CH_3$, $R_3$, $R_4=H$, $R_5=C_6H_5$ (compound 9) or $R_1=H$, $R_2=p\text{-}NO_2\text{—}C_6H_4\text{—}CH_2CH_2$, $R_3$, $R_4=H$, $R_5=C_6H_5$ (compound 10). The 2-hydroxy-morpholine derivatives 3, 6 and 10 are synthesised by the reaction of the appropriate aminoalcohol (22 mmol) and the 2-bromophenylacetophenone or the 2-bromoacetophenone (10 mmol) in ether and acetone for 15 hours at room temperature. Me 2-alkoxy derivatives 1, 4 and 7 are synthesised by the reaction of the respective 2-hydroxy derivative with the appropriate alcohol, in acid medium and reflux. Compounds 2, 5, 8 and 9 are synthesised by the reaction of the respective 2-hydroxy derivative with the 3-bromopropanol in acidic medium and reflux. The 2-(3-bromopropoxy) derivatives thin reacted with silver nitrate in acetonitrile and reflux. The compounds of formula (I) decrease significantly total cholesterol, triglyceride and LDL-cholesterol levels in plasma. The compounds of formula (I) possess potent antioxidant activity. The compounds of formula (I) with the above properties could be useful to the treatment of hypercholesterolemia, hyperlipidemia and atheromatosis.

10 Claims, No Drawings

HYPOLIPIDEMIC AND ANTIOXIDANT MORPHOLINE DERIVATIVES

The present invention relates to the synthesis of novel morpholine derivatives and the evaluation of their hypocholesterolemic, hypolipidemic and antioxidant activity. Especially, the present invention relates to the synthesis and pharmacochemical evaluation of morpholine derivatives of the formula I

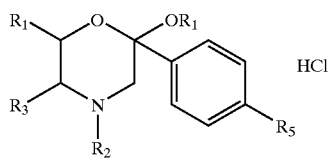

I

HCl in which $R_1=CH_2CH_3$, $R_2=CH_3$, $R_3$, $R_4=H$, $R_5=C_6H_5$ (compound 1) or $R_1=CH_2CH_2CH_2ONO_2$, $R_2=CH_3$, $R_3,R_4=H$, $R_5=C_6H_5$ (compound 2) or $R_1=H$, $R_2$13 $R_3=(CH_2)_4$, $R_4=H$, $R_5=C_6H_5$ (compound 3) or $R_1=CH_2CH_2CH_3$, $R_2-R_3=(CH_2)_4$, $R_4=H$, $R_5=C_6H_5$ (compound 4) or $R_1=CH_2CH_2CH_2ONO_2$ $R_2-R_3=(CH_2)_4$, $R_4=H$, $R_5=C_6H_5$ (compound 5) or $R_1=H$, $R_2=CH_3$, $R_3-R_4=(CH_2)_4$, $R_5=C_6H_5$ (compound 6) or $R_1=CH_2CH_2CH_3$, $R_2=CH_3$, $R_3-R_4=(CH_2)_4$, $R_5=C_6H_5$ (compound 7) or $R_1=CH_2CH_2CH_2ONO_2$, $R_2=CH_3$, $R_3-R_4=(CH_2)4$, $R_5=C_6H_5$ (compound 8) or $R_1=CH_2CH_2CH_2ONO_2$, $R_2=CH_3$, $R_3$, $R_4=H$, $R_5=H$ (compound 9) or $R_1=H$, $R_2=p-NO_2-C_6H_4-CH_2CH_2$, $R_3$, $R_4=H$, $R_5=C_6H_5$ (compound 10).

It is well known that the pathogenesis of atheromatosis is related with a lot of factors, the most important of them are:

oxidative modification of the low density lipoproteins (LDL)

increased levels of cholesterol and LDL-cholesterol in blood increased levels of triglycerides in blood decreased levels of HDL-cholesterol in blood thrombogenesis, endothelial injury and haemodynamic factors.

Especially, the oxidative modification of LDL appears to be the most risk atherogenic process, which induces inflammatory and apoptotic mechanisms and finally the formation of foam cells and fatty streaks.

At this field of research, the most of the synthetic compounds posses hypocholesterolemic or hypolipidemic or antioxidant activity. Their are no reports about compounds able to decrease total cholesterol, triglycerides and LDL-cholesterol in blood in combination with antioxidant activity.

Considering the above we think that it would be interesting to design, synthesise and evaluate compounds with hypocholesterolemic, hypolipidemic and antioxidand activity.

The novel derivatives we are reporting are able to decrease total cholesterol levels in plasma significantly. Also, the novel derivatives are able to decrease triglycerides and LDL-cholesterol levels in plasma.

The novel derivatives, except their hypolipidemic activity posses also potent antioxidant activity. We think that the combination of the hypolipidemic and the antioxidant activity is necessary for the prevention and treatment of ahteromatosis more effectively.

The present invention relates to the synthesis and the evaluation of antioxidant, hypocholesterolemic and hypolipidemic activity of novel morpholine derivatives of the general structure (I).

METHODS

Synthesis

The 2-hydroxy-morpholine derivatives 3, 6 and 10 are synthesised by the reaction of the appropriate aminoalcohol (22 mmol) and the 2-bromo4-phenylacetophenone or the 2-bromoacetophenone (10 mmol) in ether and acetone for 15 hours at room temperature. After washing with saturated solution of sodium chloride, drying with potassium carbonate, evaporation in vacuo and neutralisation with hydrochloric acid 10% in ether, the 2-hydroxy derivatives are obtained and recrystalised from acetone and ether.

The 2-alkoxy derivatives 1, 4 and 7 are synthesised by the reaction of the respective 2-hydroxy derivative with the appropriate alcohol, in acid medium and reflux.

Compounds 2, 5, 8 and 9 are synthesised by the reaction of the respective 2-hydroxy derivative with the 3-bromopropanol in acidic medium and reflux. The 2-(3-bromopropoxy) derivatives then react with silver nitrate in acetonitrile and reflux.

Scheme 1: Synthetic pathway for the morpholine

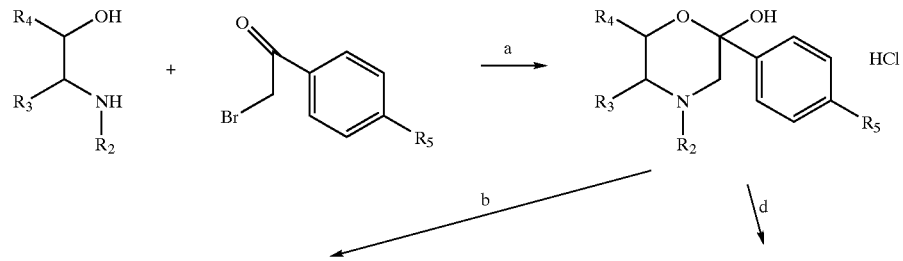

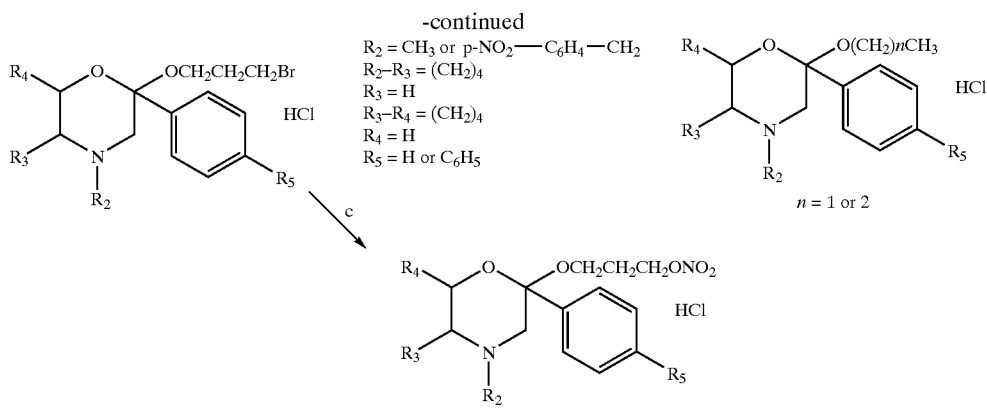

a) room temperature, HCl in ether; b) 3-bromopropanol, reflux for 3 h; c) AgNO$_3$, acetonitrile, reflux for 2 h; d) ethanol or propanol, reflux for 15 h Evaluation of the Antioxidant Activity

[Method]

The evaluation of the antioxidant activity of the novel compounds was performed in vitro by peroxidation of rat hepatic microsomal membrane lipids. Lipid peroxidation was induced by the $Fe^{2+}$/ascorbic acid system. Rat hepatic microsomes were heat-inactivated (90° C. for 90 s). A fresh solution of ascorbic acid (0.2 mM) in Tris-HCl buffer (pH 7.4) and the tested compounds, dissolved in DMSO to give final concentrations of 1 mM to 0.1 mM, were added to microsomes Equal amount of buffer was added to the control samples. The reaction was initiated by addition of FeSO$_4$ (10 $\mu$M). The mixture was incubated at 37° C. for 45 min. Aliquots were taken at various time intervals and lipid peroxidation was assessed by spectrophotometric determination of the 2-thiobarbituric acid reactive material at 535 nm.

[Results]

All tested compounds inhibited lipid peroxidation 100% at 1 mM and this action is maintained even at 0.1 mM.

Evaluation of the Hypolipidemic Activity

[Method]

The hypocholesterolemic and hypolipidemic activity of the synthesised compounds was performed by the inhibition of the hyperlipidemia induced by the Triton WR 1339 in rats. Triton WR 1339 as an intraperitoneal (i.p.) injection acts due to induction of HMG-CoA reductase. Using male Fischer rats (230–280 g) in group of five (test group), we injected a solution of 200 mg/Kg Triton WR 1339 i.p. and the same time 28 to 56 $\mu$mol/Kg of the tested compounds and probucol (as reference), suspended in aqueous solution was injected i.p. Control group was treated i.p. with Triton WR 1339 and 10 ml/Kg of the vehicle of the tested compounds i.p. After 24 hours, blood was taken from the celiac aorta and collected to heparinised tubes. Blood was centrifuged for 15 minutes at 3000 rpm and plasma was selected for the determination of total cholesterol (TC), LDL cholesterol (LDL-C) and triglycerides (TG) using commercial kits.

[Results]

Our results indicate that the tested compound decrease total cholesterol levels in plasma even by 54%, triglyceride levels even by 49% and LDL-cholesterol level even by 51% and all compounds were more potent than probucol (table 1).

The above results indicate that the novel compounds posses antioxidant and potent hypolipidemic and hypocholesterolemic action. This combination of antioxidant and hypolipidemic properties may be useful against atheromatosis.

TABLE 1

Effect of selected compounds and probucol on plasma Total Cholesterol (TC), Triglyceride (TG) and Low Density Lipoprotein (LDL) levels.

| compd | Dose ($\mu$mol/kg, ip) | Percent decrease compared to controls[*] | | |
|---|---|---|---|---|
| | | TC | TG | LDL |
| 1 | 56 | 30* | 39* | 22* |
| 3 | 56 | 22* | 20* | 51* |
| 4 | 56 | 36* | 34* | 17[NS] |
| 6 | 28 | 54** | 49* | 51* |
| 7 | 56 | 50* | 41* | 28* |
| Probucol | 56 | 18* | 11[NS] | 18[NS] |

[*]All determinations are performed at least in duplicate and SD is always within ±10% of the absorbance values.
Asterisks indicate statistical significance (Student's t-test) as follows:
**P < 0.005,
*P < 0.05,
[NS]not significant (P > 0.1).

EXAMPLES

Synthesis of Compound 1

10 mmol of the 2-hydroxy derivative was refluxed in 100ml of absolut ethanol in acidified medium by HCl in ether. After 15 h of reflux, most of the solvent was removed in vacuo and the product was crystallised with ether.

Synthesis of Compound 2

10 mmol of the 2-hydroxy derivative and 22mmol of 3-bromopropanol in acetone (30 ml) and acidic medium, were refluxed for 3 h. After 3 h the product, the 2-(3-bromopropoxy) derivative, was crystallised by ether. 10 mmol of the 2-(3-bromopropoxy) derivative reacted with 15 mmol of silver nitrate and refluxed for 2 h. After removing of the solvent in vacuo, desolving of the residue in chloroform, filtration, washing of the filtrate with water, drying of the chloroformic layer with calcium chloride, removing of the chloroform in vacuo, neutralisation with hydrobromic acid in ether and crystallisation by ether, the final product was obtained.

Synthesis of Compound 3

22 mmol of 2-hydroxymethylpiperidine reacted with 10 mmol of 2-bromo4-phenylacetophenone in ether and acetone for 15 h at room temperature. After washing with satureted solution of sodium chloride drying with potassium carbonate, evaporation in vacuo and neutralisation with hydrochloric acid 10% in ether, compound 3 was obtained and was recrystalised from acetone and ether.

Synthesis of Compound 4

10 mmol of compound 3 was refluxed in 100 ml of n-propanol in acidic medium by HCl in ether. After 15 h of reflux the solvent was removed in vacuo and the product was crystallised with ether.

Synthesis of Compound 5

10 mmol of compound 3 and 22 mmol of 3-bromopropanol in acetone (30 ml) in acidic medium, were refluxed for 3 h. After 3 h the product, the 2-(3-bromopropoxy) derivative, was crystallised with ether. 10 mmol of the 2-(3-bromopropoxy) derivative reacted with 15 mmol of silver nitrate and refluxed for 2 h. After removing of the solvent in vacuo, desolving of the residue in chloroform, filtration, washing of the filtrate with water, drying of the chloroformic layer with calcium chloride, removing of the chloroform in vacuo, neutralisation with hydrobromic acid in ether and crystallisation by ether, the final product was obtained.

Synthesis of Compound 6

22 mmol of N-methylamino-cyclohexanol-2 reacted with 10 mmol of 2-bromo4-phenylacetophenone in ether and acetone for 15 h at room temperature. After washing with satureted solution of sodium chloride, drying with potassium carbonate, evaporation in vacuo and neutralisation with hydrochloric acid 10% in ether, compound 3 was obtained and was recrystalised from acetone-ether.

Synthesis of Compound 7

10 mmol of compound 6 was refluxed in 100 ml of n-propanol in acidic medium by HCl in ether. After 15 h of reflux the solvent was removed in vacuo and the product was crystallised with ether.

Synthesis of Compound 8

10 mmol of compound 6 and 22 mmol of 3-bromopropanol in acetone (30 ml) and acidic medium, were refluxed for 3 h. After 3 h the product, the 2-(3-bromopropoxy) derivative, was crystallised in ether. 10 mmol of the 2-(3-bromopropoxy) derivative reacted with 15 mmol of silver nitrate and reflux for 2 h. After removing of the solvent in vacuo, desolving of the residue in chloroform, filtration, washing of the filtrate with water, drying of the chloroformic layer with calcium chloride, removing of the chloroform in vacuo, neutralisation with hydrobromic acid in ether and crystallisation by ether, the final product was obtained.

Synthesis of Compound 9

10 mmol of the 2-hydroxy derivative and 22 mmol of 3-chloropropanol in acetone (30 ml) and acidic medium, were refluxed for 3 h. After 3 h the product, the 2-(3-bromopropoxy) derivative, was crystallised in ether. 10 mmol of the 2-(3-bromopropoxy) derivative reacted with15 mmol of silver nitrate and refluxed for 2 h. After removing of the solvent in vacuo, desolving of the residue in chloroform, filtration, washing of the filtrate with water, drying of the chloroformic layer with calcium chloride, removing of the chloroform in vacuo, neutralisation with hydrobromic acid in ether and crystallisation by ether, the final product was obtained.

Synthesis of Compound 10

22 mmol of p-nitro-phenethylaminoethanol reacted with 10 mmol of 2-bromo4-phenylacetophenone in ether and acetone for 15 h at room temperature. After washing with satureted solution of sodium chloride, drying with potassium carbonate, evaporation in vacuo and neutralisation with hydrochloric acid 10% in ether, compound 3 was obtained and was recrystalised from acetone-ether.

What is claimed is:

1. A compound of formula I

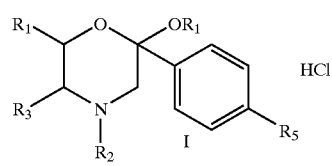

FORMULA I in which [[$R_1$=$CH_2CH_3$, $R_2$=$CH_3$, $R_3$, $R_4$=H, $R_5$=$C_6H_5$ (compound 1)or]]

$R_1$=$CH_2CH_2CH_2ONO_2$, $R_2$=$CH_3$, $R_3$, $R_4$=H, $R_5$=$C_6H_5$ (compound 2) or $R_1$=H, $R_2$—$R_3$=$(CH_2)_4$, $R_4$=H, $R_5$=$C_6H_5$ (compound 3) or $R_1$=$CH_2CH_2CH_3$, $R_2$—$R_3$=$(CH_2)_4$, $R_4$=H, $R_5$=$C_6H_5$ (compound 4) or $R_1$=$CH_2CH_2CH_2ONO_2$, $R_2$—$R_3$=$(CH_2)_4$, $R_4$=H, $R_5$=$C_6H_5$ (compound 5) or $R_1$=H, $R_2$=$CH_3$, $R_3$—$R_4$=$(CH_2)_4$, $R_5$=$C_6H_5$ (compound 6) or $R_1$=$CH_2CH_2CH_3$, $R_2$=$CH_3$, $R_3$—$R_4$=$(CH_2)_4$, $R_5$=$C_6H_5$ (compound 7) or $R_1$=$CH_2CH_2CH_2ONO_2$, $R_2$=$CH_3$, $R_3$—$R_4$=$(CH_2)_4$, $R_5$=$C_6H_5$ (compound 8) or $R_1$=$CH_2CH_2CH_2ONO_2$, $R_2$=$CH_3$, $R_3$—$R_4$=H, $R_5$=H (compound 9) or $R_1$=H, $R_2$=P-$NO_2$—$C_6H_4$—$CH_2CH_2$, $R_3$, $R_4$=H, $R_5$=$C_6H_5$ (compound 10).

2. The compound of claim 1, wherein $R_1$=$CH_2CH_2CH_2ONO_2$, $R_2$=$CH_3$, $R_3$, $R_4$=H, $R_5$=$C_6H_5$.

3. The compound of claim 1, wherein $R_1$=H, $R_2$—$R_3$=$(CH_2)_4$, $R_{4=H,\ R5}$=$C_6H_5$.

4. The compound of claim 1, wherein $R_1$=$CH_2CH_2CH_3$, $R_2$—$R_3$=$(CH_2)_4$, $R_4$=H, $R_5$=$C_6H_5$.

5. The compound of claim 1, wherein $R_1$=$CH_2CH_2CH_2ONO_2$, $R_2$—$R_3$=$(CH_2)_4$, $R_4$=H, $R_5$=$C_6H_5$.

6. The compound of claim 1, wherein $R_1$=H, $R_2$=$CH_3$, $R_3$—$R_4$=$(CH_2)_4$, $R_5$=$C_6H_5$.

7. The compound of claim 1, wherein $R_1$=$CH_2CH_2CH_3$, $R_2$=$CH_3$, $R_3$—$R_4$=$(CH_2)_4$, $R_5$=$C_6H_5$.

8. The compound of claim 1, wherein $R_1$=$CH_2CH_2CH_2ONO_2$, $R_2$=$CH_3$, $R_3$—$R_4$=$(CH_2)_4$, $R_5$=$C_6H_5$.

9. The compound of claim 1, wherein $R_1$=$CH_2CH_2CH_2ONO_2$, $R_2$=$CH_3$, $R_3$—$R_4$=H, $R_5$=H.

10. The compound of claim 1, wherein $R_1$=H, $R_2$=p-$NO_2$—$C_6H_4$—$CH_2CH_2$, $R_3$, $R_4$=H, $R_5$=$C_6H_5$.

* * * * *